United States Patent
Abernethy et al.

(10) Patent No.: US 12,383,550 B2
(45) Date of Patent: Aug. 12, 2025

(54) OPIOID OVERDOSE REVERSAL MIXTURES

(71) Applicants: John Abernethy, Gainesville, FL (US); Georgiy Nikonov, Gainesville, FL (US); Michael Voronkov, Somerville, MA (US)

(72) Inventors: John Abernethy, Gainesville, FL (US); Georgiy Nikonov, Gainesville, FL (US); Michael Voronkov, Somerville, MA (US)

( * ) Notice: Subject to any disclaimer, the term of this patent is extended or adjusted under 35 U.S.C. 154(b) by 0 days.

(21) Appl. No.: 17/803,164

(22) Filed: Mar. 11, 2022

(65) Prior Publication Data

US 2024/0009184 A1    Jan. 11, 2024

(51) Int. Cl.
*A61K 31/485*        (2006.01)
*A61P 25/36*         (2006.01)

(52) U.S. Cl.
CPC .......... *A61K 31/485* (2013.01); *A61P 25/36* (2018.01)

(58) Field of Classification Search
CPC .............................. A61K 31/485; A61P 25/36
See application file for complete search history.

(56) References Cited

U.S. PATENT DOCUMENTS

| | | | |
|---|---|---|---|
| 2004/0180916 A1* | 9/2004 | Levine | A61P 25/04 514/282 |
| 2020/0055864 A1* | 2/2020 | Nikonov | C07C 219/28 |
| 2020/0246253 A1* | 8/2020 | Boyer | A61K 9/0056 |

OTHER PUBLICATIONS

Yokell MA, Zaller ND, Green TC, McKenzie M, Rich JD. Intravenous use of illicit buprenorphine/naloxone to reverse an acute heroin overdose. J Opioid Manag. Jan.-Feb. 2012;8(1):63-66. doi: 10.5055/jom.2012.0098. PMID: 22479887; PMCID: PMC3343634. (Year: 2012).*
Wang S. Historical Review: Opiate Addiction and Opioid Receptors. Cell Transplant. Mar. 2019;28(3):233-238. doi: 10.1177/0963689718811060. Epub Nov. 13, 2018. PMID: 30419763; PMCID: PMC6425114. (Year: 2019).*
Body Measurements. National Center for Health Statistics, Print, Center for Disease Control and Prevention. Sep. 10, 2021 (Year: 2021) p. 1.*
Kloxxado Dosage, Drugs.com, May 10, 2022 (Year: 2022) p. 1-3.*
Narcan Dosage, Drugs.com, Oct. 24, 2022 (Year: 2022) p. 1-3.*

* cited by examiner

*Primary Examiner* — Kortney L. Klinkel
*Assistant Examiner* — Richard Grant Peckham
(74) *Attorney, Agent, or Firm* — Ted Whitlock; Ted Whitlock Registered Patent Attorney PA

(57) ABSTRACT

The invention presented is a remedial opioid overdose mixture that includes a therapeutically effective dose of an opioid receptor antagonist; and, a therapeutically effective dose of an opioid receptor agonist. In one embodiment, the opioid receptor antagonist is naloxone while the opioid receptor agonist is nalbuphine. One specific naloxone derivative is NX-90 and a specific nalbuphine derivative is NB-33. The mixture can be administered intranasally, intravenously and by autoinjector. In some dose mixtures, reversal time is about three minutes.

12 Claims, 3 Drawing Sheets

OPIOID OVERDOSE REVERSAL MIXTURES

FIELD OF THE INVENTION

The present invention relates to opioid derived compositions, used in reversing opioid overdose.

BACKGROUND

Naloxone, sold under the brand name Narcan, among other names, is a medication used to block the effects of opioids, especially in overdose situations. Naloxone may also be combined with an opioid (in the same pill or compound), to decrease the risk of opioid misuse. For instance, it can be added to the coating for a sustained release opiate Compound, to prevent crushing of the sustained release compound, which could lead to an overdose.

When given intravenously, naloxone typically works within two minutes, and when injected into a muscle, it works within five minutes. It may also be sprayed into the nose. The effects of naloxone typically last for about half an hour to an hour. Thus, multiple doses and administration of naloxone may be required, as the duration of action of most opioids is greater than that of naloxone.

Administration of naloxone to opioid-dependent individuals may cause symptoms of opioid withdrawal, such as, for example, restlessness, agitation, nausea, vomiting, increased heart rate and perspiration. To prevent this, small doses of naloxone can be given every few minutes until the desired effect is reached.

In the individuals with prior history of heart disease or persons who take medications that negatively affect the heart, further heart problems have occurred. Naloxone appears to be safe in pregnancy, after having been given to and tested on a limited number of subjects.

Naloxone is a non-selective and competitive opioid receptor antagonist. It works by reversing the depression of the central nervous system and respiratory system caused by opioids.

Naloxone, also known as N-allylnoroxymorphone or as 17-allyl4,5α-epoxy-3,14-dihydroxymorphinan-6-one, is a synthetic morphinan derivative and was derived from oxymorphone (14-hydroxydihydromorphinone), an opioid analgesic. Oxymorphone, in turn, was derived from morphine, an opioid analgesic and naturally occurring constituent of the opium poppy.

Naloxone is a racemic mixture of two enantiomers, (−)-naloxone (levonaloxone) and (+)-naloxone (dextronaloxone), only the former of which is active at opioid receptors. The drug is a highly lipophilic, allowing it to rapidly penetrate the brain and to achieve a far greater brain to serum ratio than that of morphine. Opioid antagonists related to naloxone include cyprodime, nalmefene, nalodeine, naloxol, and naltrexone.

The chemical half-life of naloxone is such that injection and nasal forms have been marketed with 24-month and 18-month shelf-lives, respectively. A 2018 study noted that the nasal and injection forms presented as chemically stable to 36- and 28-months, respectively, which prompted an as yet incomplete five-year stability study to be initiated. This suggests that expired caches of material in community and healthcare settings may still be efficacious substantially beyond their labeled expiration dates.

Certain articles about opioid antagonists emphasize the shortcomings and problems with currently known formulations, and the need for an improved and more stable compound that may be used safely on patients suffering from opioid addiction.

An article by Adam Bisaga, entitled "What Should Clinicians Do As Fentanyl Replaces Heroin?" (published in Addiction, Vol. 114, pp. 781-86, at worldwide website: onlinelibrary.wiley.com/doi/epdf/10.1111/add.14522) describes that high affinity antagonists may not suffice to block effects of fentanyl and their higher doses that broader concerns over systematic safety may be required. Furthermore, fentanyl overdose prevention requires higher doses of naloxone and repeated dosing that is encumbered by much shorter overdose prevention window for fentanyl than heroin.

Roger Chou et al. describes in the article entitled "Management of Suspected Opioid Overdose With Naloxone by Emergency Medical Services Personnel" (published at In Comparative Effectiveness Review No. 193, at worldwide website: effectivehealthcare.ahrq.gov/sites/default/files/pdf/cer-193-naloxone-final_1.pdf) that existing dosing guidelines of naloxone may not be sufficient to prevent overdose by fentanyl and fentanyl analogues.

Rachael Rzasa Lynn et al. describes in the article entitled "Naloxone Dosage for Opioid Reversal: Current Evidence and Clinical Implications" (published in Therapeutic Advances in Drug Society Review, Vol. 9 (1), pp. 63-88, 2018 at worldwide website: ncbi.nlm.nih.gov/pmc/articles/PMC5753997/pdf/10.1177_2042098617744161.pdf) that double dose of naloxone administered to patient anesthetized with fentanyl produced no improvement in oxygen intake, while quadruple dose of naloxone produced significant improvements. Further she teaches that the interactions between the opioid agonist/antagonist and the mu-opioid receptor may be the greatest determinant of the speed of recovery from the respiratory effects of many opioids, which may not markedly accelerate with increasing doses of naloxone, but rather respond to a minimum effective dose, while for compounds like buprenorphine, higher doses of naloxone may even lose efficacy. She also cites numerous reports describing fentanyl overdoses as initially unresponsive to IN (intranasal) naloxone and only transiently reversed with IV (intravenous) naloxone (if at all), requiring additional IV doses or continuous infusions to prevent recurrence of toxicity and respiratory depression.

I. A. Elkiweri et al. describes in the article entitled "Competitive substrates for P-glycoprotein and organic anion protein transporters differentially reduce blood organ transport of fentanyl and loperamide: pharmacokinetics and pharmacodynamics in Sprague-Dawley rats" (published online in 2009) at worldwide website: ncbi.nlm.nih.gov/pubmed/19095843) that naloxone and fentanyl share a transporter for cellular influx that becomes saturated by a high plasma concentration of fentanyl, preventing rapid influx of naloxone across the BBB (blood brain barrier) regardless of dose.

Rebecca McDonald et al. describes in the article entitled "Pharmacokinetics of concentrated naloxone nasal spray for opioid overdose reversal: Phase I healthy volunteer study" (published in Addiction, 113, pp. 484-93 at_) that high concentration (2 mg) naloxone intranasal (i.n.) spray has early absorption rate that is comparable to intramuscular (i.m.) 0.4 mg injection and could be used as a take-home antidote. He suggests that high dose i.n. (intranasal) naloxone could be given without risk of "overantagonism".

Baohua Huang et al. describes in the article entitled "Human plasma-mediated hypoxic activation of indolequinone-based naloxone pro-drugs" (published in Bioorganic &

Medicinal Chemistry Letters in 2009, 19(17), 5016-5020) that indolequinone based naloxone pro-drug can reverse opiate induced hypoxia as a system that provides a potential means for feedback control to counter critical respiratory depression induced by narcotic analgesics. I. Ukrainets et al. discloses in the publication Chemistry of Heterocyclic Compounds (2009), 45(4), pp. 405-416) studies of 3-O-acyl derivatives of naloxone as its potential prodrugs to prevent morphine intoxication and block analgesic properties.

I. Romanov et al. describes in the Russian Patent Publication (RU 2221566—published Jan. 20, 2004) that esters of N-substituted 14-hydroxymorphinans could be used as highly effective low toxic and anti-relapse agent with prolonged morphine protective effect being after a single subcutaneous (s.c.) or i.m. injection when mixed or suspended in natural oils.

Neale (2015) describes reports of adverse reaction to naloxone inducing acute precipitation of withdrawal symptoms such as shaking, headaches and vomiting, sometimes lasting several days.

Cline (2020) reports that naloxone causes severe withdrawal symptoms and promotes of riskier drug use to mitigate painful aspects of the withdrawal.

Nalbuphine (Nubain) was launched in 1979 as an analgesic for moderate to severe pain and has effectively been used in the clinic since. It is primarily used in conjunction with anesthetics for pre- and post-operative analgesia and in labor and delivery for acute and chronic pain management. Recently its uses have been expanded to the treatment of locomotive disorders, dermatological conditions such as pruritus and addiction management.

It has also been recently shown that nalbuphine could prevent opiate tolerance and dependence in chronic pain management. It is the only narcotic analgesic of its type that is not subject to the Controlled Substances Act, an indication of its safe utility. Nalbuphine has a low oral bioavailability.

Furthermore, literature describes use of nalbuphine to address side effects of opioids. Thus Wang (1998) teaches that coadministration of either nalbuphine or naloxone with epidural morphine reduces the incidence of morphine-related side effects. Lee (1997) reported that administration of nalbuphine or naloxone with morphine dose-dependently blocked the development of morphine tolerance and dependence in rats. Kendrick (1996) demonstrated that either naloxone and nalbuphine provided good relief for pruritus in patients receiving epidural morphine. Freye (1985) reported that in apnea due to fentanyl anesthesia, the level of response of the respiratory center to CO2 was below controls after 60 min when treated with nalbuphine (0.1 mpk). Bailey P L; (1987) teaches that no patient required more than three doses (0.24 mg IV) of naloxone or four doses (10 mg; 2.5 mg IV every 2 min) of nalbuphine to reverse fentanyl induced respiratory depression. Schaer (1987) teaches that naloxone 0.05 mg or nalbuphine 10 mg or 20 mg iv can reverse fentanyl induced respiratory suppression.

However, Bailey (1986) demonstrated that nalbuphine (0.21 mpk, iv) either further depressed or did not affect respiratory drive suppression by morphine in humans.

Naloxone and nalbuphine together have been used to improve the quality of analgesia. More specifically, Gear et al (2014) teaches that agonist-antagonist opioid analgesics that produce their analgesic effect via action on the kappa-opioid receptor, produce a delayed-onset anti-analgesia in men but not women, an effect blocked by coadministration of a low dose of naloxone. Coadministration of nalbuphine with naloxone in a dose ratio of 12.5:1 blocked anti-analgesia but not analgesia. Gear (2013) also teaches that naloxone (0.4 mg) followed 5-11 minutes later by a nalbuphine infusion (5 mg/70 kg) to humans selectively blocks the actions of nalbuphine in brain regions associated with pain, leaving the analgesic-like actions intact. Kshirsagar (2008) teaches that in patients after surgical removal of one or more mandibular third molar teeth, the nalbuphine dose required to reduce early pain by 50% (ED50) was established. to be 5.85 mg and the naloxone dose required to reduce late phase pain by 50% was established to be 0.5 mg when used in combination. Gear (2003) further teaches that dose ratio is important in maximizing naloxone enhancement of nalbuphine analgesia in humans. Thus, dose ratio of 12.5:1 (i.e., 5 mg nalbuphine:0.4 mg naloxone or 2.5 mg nalbuphine:0.2 mg naloxone) resulted in analgesic enhancement, but a dose ratio of 6.25:1 (2.5 mg:0.4 mg) did not. Gordon (2007) demonstrated pain reduction in four patients with the fixed dose of 5 mg nalbuphine/0.4 mg naloxone. Schmidt (2003) reported marked decrease in pain following administration of the nalbuphine and naloxone combination.

None of these cited publications describes naloxone combination with nalbuphine or their pharmaceutically relevant salts and esters as well as prodrugs, to reverse side-effects of opioid administration when administered to a person.

NB-33 is a 3-hexadienoate derivative of nalbuphine that converts to the parent drug in a biological matrix.

NX-90 is a 3-hexadienoate derivative of naloxone that converts to the parent drug in a biological matrix.

SUMMARY OF THE INVENTION

The present invention broadly comprises a remedial opioid overdose mixture comprising: a therapeutically effective dose of an opioid receptor antagonist; and, a therapeutically effective dose of a dual opioid receptor agonist/antagonist. The mixture is applied intranasally, intramuscularly or by an injection (e.g., intravenously) to an opioid overdose patient. The remedial mixture reverses the opioid overdose in the patient. In one embodiment, the opioid receptor antagonist is naloxone and the opioid receptor agonist/antagonist is nalbuphine. In another embodiment, the overdose mixture reverses opioid overdose in about up to three minutes.

The present invention also broadly comprises a remedial opioid overdose mixture that comprises: a therapeutically effective dose of a 3-hexadienoate derivative of naloxone (NX-90) as an opioid receptor antagonist; and, a therapeutically effective dose of a 3-hexadienoate derivative of nalbuphine (NB-33) an opioid receptor agonist/antagonist. The opioid overdose mixture is applied intranasally, intramuscularly or by an injection (e.g., intravenously) to an opioid overdose patient. The remedial opioid overdose mixture reverses the opioid overdose in the patient in about up to three minutes.

One object of the invention is to supply an opioid overdose mixture that will reverse the effects of opioid overdose in about up to three minutes.

A second object of the invention is to make available an opioid overdose mixture that reverses fentanyl overdose in about three minutes.

A third object of the invention is to provide an opioid overdose mixture that can be administered intranasally, intravenously and injection (e.g., intravenously).

BRIEF DESCRIPTION OF THE SEVERAL VIEWS OF THE DRAWINGS

The nature and mode of the operation of the present invention will now be more fully described in the following detailed description of the invention taken with the accompanying drawing Figures, in which.

DETAILED DESCRIPTION OF EMBODIMENTS OF THE INVENTION

Figure 1:
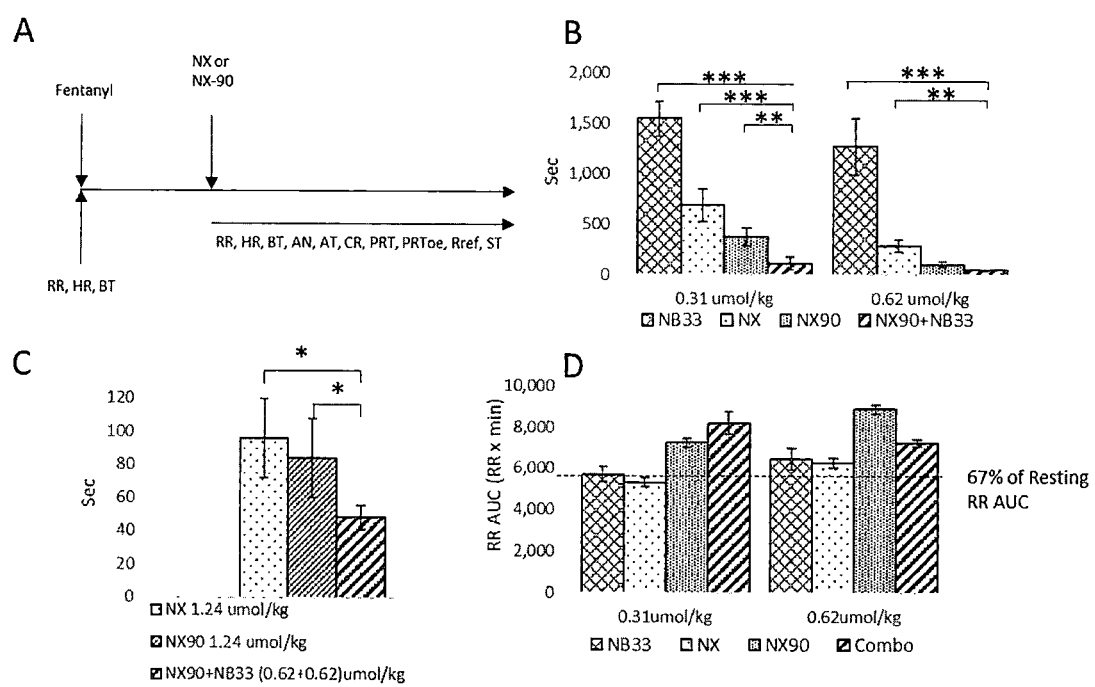
FIG. 1 is a collection of four graphs showing the results of measurements of the effects of pharmacological substances on vital signs and reflexes.

At the outset, it should be appreciated that like drawing numbers on different drawing views identify identical structural elements of the invention. It also should be appreciated that figure proportions and angles are not always to scale in order to clearly portray the attributes of the present invention.

While the present invention is described with respect to what is presently considered to be the preferred embodiments, it is understood that the invention is not limited to the disclosed embodiments. The present invention is intended to cover various modifications and equivalent arrangements included within the spirit and scope of the appended claims.

While the present invention is described with respect to what is presently considered to be the preferred embodiments, it is understood that the invention is not limited to the disclosed embodiments. The present invention is intended to cover various modifications and equivalent arrangements included within the spirit and scope of the appended claims.

Furthermore, it is understood that this invention is not limited to the particular methodology, materials and modifications described and as such May, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. It should be appreciated that the term "substantially" is synonymous with terms such as "nearly", "very nearly", "about", "approximately", "around", "bordering on", "close to", "essentially", "in the neighborhood of", "in the vicinity of", etc., and such terms may be used interchangeably as appearing in the specification and claims. It should be appreciated that the term "proximate" is synonymous with terms such as "nearby", "close", "adjacent", "neighboring", "immediate", "adjoining", etc., and such terms may be used interchangeably as appearing in the specification and claims. Although any methods, devices or materials similar or equivalent to those described herein can be used in the practice or testing of the invention, the preferred methods, devices, and materials are now described.

The present invention and at least one composition compound that is formulated based on the present invention, as for example NB-33 or NX-90 (or others) may be utilized for the treatment of side effects of opioid agonists including but not limiting to pruritus, respiratory suppression, lower body temperature, lower heart rate, loss of reflexes (e.g., corneal) and overdose.

Surprisingly, 3-hexadienoate derivative of a Nalbuphine at intranasal doses 0.22 mpk and 0.44 mpk (0.037 mpk and 0.073 mpk respectively in human equivalents) restored respiratory rate in fentanyl-overdosed rats within 30 min similar to the lowest dose of Naloxone (Example 1).

Unexpectedly, NX-90 produced a much quicker fentanyl overdose reversal in rats than the parent drug. Furthermore, animal-to-animal variation was significantly smaller in NX-90 treated group at all equimolar doses (Example 1).

Unexpectedly, co-administration of mu-antagonist (e.g., NX-90) with kappa agonist (e.g., NB-33) produced a synergistic effect in reversal of fentanyl overdose that was characteristic by shorter Total recovery times and smaller animal-to-animal variation. The efficacy against non-heroin overdose, speed of recovery and more universal response of subjects to intranasal administration is crucial to preventing overdose in street settings by the first responders, police and opiate users and offers significant advantage over current therapeutic options.

Surprisingly, co-administration of mu-antagonist (e.g., NX-90) with kappa agonist (e.g., NB-33) to an overdose subject mitigated opioid overdose non-respiratory sides effects (Example 2).

In some embodiments, the mitigated non-respiratory side effects are associated with catecholamine release (e.g., cardiovascular stimulation, pulmonary edema etc.)

In other embodiments, the mitigated non-respiratory side effects are associated with pain aspect of acute withdrawal and prevents post-discharge risky behavior.

In one embodiment of the present invention, NX-90 is used to reverse opioid overdose.

In another embodiment of the present invention, NX-90 is used to reverse opioid other than heroin overdose.

In another embodiment of the present invention, NX-90 is used intranasally

In another embodiment of the present invention, NX-90 is used in doses 0.005 mpk to 0.5 mpk in humans.

In another embodiment of the present invention, NX-90 is used in doses 0.022 mpk to 0.087 mpk in humans.

In one embodiment of the present invention, NB-33 is used to reverse opioid overdose.

In another embodiment of the present invention, NB-33 is used to reverse opioid other than heroin overdose.

In another embodiment of the present invention, NB-33 is used intranasally

In another embodiment of the present invention, NB-33 is used in doses 0.005 mpk to 0.5 mpk in humans.

In another embodiment of the present invention, NB-33 is used in doses 0.022 mpk to 0.087 mpk in humans.

Yet in another embodiment of the present invention, a combination of opioid receptor antagonist and kappa-agonist is used to reverse opioid overdose.

In another embodiment of the present invention, a combination of opioid receptor antagonist and kappa-agonist is used to reverse opioid other than heroin overdose.

In another embodiment of the present invention, a combination of opioid receptor antagonist and kappa-agonist is administered intranasally.

In another embodiment of the present invention, a combination of opioid receptor antagonist and kappa-agonist is used in doses 0.005 mpk to 0.5 mpk in humans.

In another embodiment of the present invention, a combination of opioid recepto3 antagonist and kappa-agonist is used in doses 0.022 mpk to 0.087 mpk in humans.

Yet in one more embodiment of the present invention, a combination of opioid receptor antagonist selected from NX-90 or Naloxone and kappa-agonist selected from NB-33 or Nalbuphine is used to reverse opioid overdose.

In another embodiment of the present invention, a combination of opioid receptor antagonist selected from NX-90 or Naloxone and kappa-agonist selected from NB-33 or Nalbuphine is used to reverse opioid other than heroin overdose.

Yet in another embodiment of the present invention, a combination of opioid receptor antagonist selected from NX-90 or Naloxone and kappa-agonist selected from NB-33 or Nalbuphine is used intranasally.

In another embodiment of the present invention, a combination of opioid receptor antagonist selected from NX-90 or Naloxone and kappa-agonist selected from NB-33 or Nalbuphine is used intravenously.

In another embodiment of the present invention, a combination of opioid receptor antagonist selected from NX-90 or Naloxone and kappa-agonist selected from NB-33 or Nalbuphine is used in doses 0.005 mpk to 0.5 mpk in humans.

In another embodiment of the present invention, a combination of opioid receptor antagonist selected from NX-90 or Naloxone and kappa agonist selected from NB-33 or Nalbuphine is used in doses 0.022 mpk to 0.087 mpk in humans.

Yet in one embodiment of the present invention, a combination of NX-90 and NB-33 is used to reverse opioid overdose.

In another embodiment of the present invention, a combination of NX-90 and NB-33 is used to reverse opioid overdose other than heroin overdose.

In another embodiment of the present invention, a combination of NX-90 and NB-33 is used intranasally.

In another embodiment of the present invention, a combination of NX-90 and NB-33 is used in doses ranging from 0.005 mpk to 0.5 mpk in humans.

In another embodiment of the present invention, a combination of NX-90 and NB-33 is used in doses ranging from 0.022 mpk to 0.087 mpk in humans.

In all cases it is understood that the above-described examples and compounds are merely illustrative of the many possible specific embodiments which represent applications of the present invention. Numerous and varied other arrangements can be readily devised in accordance with the principles of the present invention without departing from the spirit and the scope of the invention.

In another embodiment, the present invention could also be practiced with other kappa-agonists such as, but not limited to, Nalbuphine, Pentazocine, Butorphanol or related compounds or mu-antagonists such as, but not limited to Naltrexone, Naloxone or related compounds.

In a further one or more embodiments, the present invention is can be practiced with combination of mu-antagonists with kappa-agonists as well as their esters in pharmaceutically acceptable salts to reverse overdose when given intravenously, intranasally, transdermally, sublingually, rectally, topically, intramuscularly, subcutaneously or via inhalation.

Example 1. Efficacy Assessment of Combinations (e.g., NX90+NB33, NX+NB) vs Naloxone in Fentanyl Driven Overdose Animals Clinical monitoring, respectively clinical evaluation was performed in all stages of the study before and after the administration of pharmacological substances: for Fentanyl (FT), and test articles (e.g., Naloxone (NX), Nalbuphine (NB), NX90, NB33) before treatment and one hour after treatment (2 minute intervals within the first 10 minutes and then at 10-minute interval).

The rats from each group were treated with Fentanyl, IM (intramuscular), at the set dose (0.130 mg/kg). After sedation/analgesia were installed, a test article was administered IN (intranasally) at the specific dose. The doses of test articles used ranged from 0.31 umol/kg to 1.24 umol/kg (of body weight). Before treatment and one hour after treatment with test article, monitoring was performed at 2 minute intervals within the first 10 minutes and then at 10 minute intervals. The rats were monitored individually—RR, HR, BRT, and AN, AT, CR, PRT, PRToe, RRfe, ST.

The time period required to induce fentanyl overdose was measured from administration to suppression of all monitored reflexes and a significant reduction in respiratory (risk of respiratory arrest) and cardiac frequency. At that time, the test article was administered intranasally and began recording the time required for complete recovery of all reflexes, and consequent increase in heart rate and respiratory rate.

Total recovery time was defined as time needed to return all overdose parameters (RR, HR, AN—Alertness, AT—Astazia, CR—Corneal reflex, PRT—Pinch reflex tail, PRToe—Pinch reflex toe, Rref—Righting reflex, ST—Sternal recumbency) to normal physiological values and at least of 67% of resting respiratory rate.

FIG. 1 is a collection of four graphs showing the results of measurements of the effects of pharmacological substances on vital signs and reflexes. A. shows the design of the experiment and the vitals and reflexes monitored: RR—respiratory rate, HR—heart rate, BT—body temperature, AN—alertness, AT—astazia, CR—corneal reflex, PRT—pinch reflex tail, PRToe—pinch reflex toe, Rref—righting reflex, ST—sternal recumbency.

B. depicts the mean time to all reflexes restored at 0.31 and 0.62 umol/kg doses, while C. shows the mean time to all reflexes restored at 1.24 umol/kg doses. D. illustrates RR AUC (RR×min) for each treated group. Resting RR AUC was calculated by multiplying average resting RR by 60 min.

TABLE 1

| | | | | | | | | | | |
|---|---|---|---|---|---|---|---|---|---|---|
| Naloxone testing and recovery time evaluation | | | | | | | | | | |
| Group | Tested dose umol/kg (mpk) | Rat no. | Sex | Body weight (kg) | Fentanyl Dose/rat (mg) | Overdose induction (seconds) | Average overdose time (seconds) | Dose/rat NX90:NB33 (0.4 mg:0.4 mg) (mg) | ml of diluted NX90:NB33 IN | Total recovery time (seconds) | Average total recovery time (seconds) |
| NX 1 | 0.16 (0.1) | 1 | M | 0.271 | 0.0352 | 180 | 168 (2 min and 48 sec) | 0.0271 | 0.0678 | 420 | 684 ± 356 |
| | | 2 | F | 0.235 | 0.0306 | 60 | | 0.0235 | 0.0588 | 540 | |
| | | 3 | F | 0.243 | 0.0316 | 240 | | 0.0243 | 0.0608 | 1200 | |
| | | 4 | M | 0.243 | 0.0316 | 180 | | 0.0243 | 0.0608 | 900 | |
| | | 5 | F | 0.220 | 0.0286 | 180 | | 0.0220 | 0.0550 | 360 | |

TABLE 1-continued

Naloxone testing and recovery time evaluation

| Group | Tested dose umol/kg (mpk) | Rat no. | Sex | Body weight (kg) | Fentanyl Dose/rat (mg) | Overdose induction (seconds) | Average overdose time (seconds) | Dose/rat NX90:NB33 (0.4 mg:0.4 mg) (mg) | ml of diluted NX90:NB33 IN | Total recovery time (seconds) | Average total recovery time (seconds) |
|---|---|---|---|---|---|---|---|---|---|---|---|
| NX 2 | 0.32 (0.2) | 1 | M | 0.358 | 0.0465 | 120 | 132 (2 min and 12 sec) | 0.0716 | 0.1790 | 300 | 288 ± 130 |
|  |  | 2 | M | 0.327 | 0.0425 | 60 |  | 0.0654 | 0.1635 | 480 |  |
|  |  | 3 | F | 0.329 | 0.0428 | 240 |  | 0.0658 | 0.1645 | 120 |  |
|  |  | 4 | M | 0.415 | 0.0540 | 120 |  | 0.0830 | 0.2075 | 300 |  |
|  |  | 5 | F | 0.304 | 0.0395 | 120 |  | 0.0608 | 0.1520 | 240 |  |

TABLE 2

NX90 testing and recovery time evaluation

| Group | Tested dose umol/kg (mpk) | Rat no. | Sex | Body weight (kg) | Fentanyl Dose/rat (mg) | Overdose induction (seconds) | Average overdose time (seconds) | Dose/rat NX90:NB33 (0.4 mg:0.4 mg) (mg) | ml of diluted NX90:NB33 IN | Total recovery time (seconds) | Average total recovery time (seconds) |
|---|---|---|---|---|---|---|---|---|---|---|---|
| NX90 1 | 0.16 (0.13) | 1 | F | 0.261 | 0.0339 | 240 | 288 (4 min and 48 sec) | 0.0339 | 0.0424 | 360 | 372 ± 201 |
|  |  | 2 | M | 0.270 | 0.0351 | 360 |  | 0.0351 | 0.0439 | 240 |  |
|  |  | 3 | M | 0.274 | 0.0356 | 360 |  | 0.0356 | 0.0445 | 720 |  |
|  |  | 4 | F | 0.263 | 0.03.42 | 360 |  | 0.0342 | 0.0427 | 240 |  |
|  |  | 5 | M | 0.278 | 0.0361 | 120 |  | 0.0361 | 0.0452 | 300 |  |
| NX90 2 | 0.32 (0.26) | 1 | M | 0.398 | 0.0517 | 120 | 312 (5 min and 12 sec) | 0.1035 | 0.1294 | 60 | 102 ± 58 |
|  |  | 2 | M | 0.374 | 0.0486 | 480 |  | 0.0972 | 0.1216 | 30 |  |
|  |  | 3 | F | 0.344 | 0.0447 | 360 |  | 0.0894 | 0.1118 | 120 |  |
|  |  | 4 | F | 0.384 | 0.0499 | 240 |  | 0.0998 | 0.1248 | 180 |  |
|  |  | 5 | M | 0.385 | 0.0501 | 360 |  | 0.1001 | 0.1251 | 120 |  |
| NX90 3 | 0.64 (0.52) | 1 | M | 0.249 | 0.0324 | 240 | 228 (3 min and 48 sec) | 0.1295 | 0.1619 | 180 | 84 ± 54 |
|  |  | 2 | F | 0.221 | 0.0287 | 360 |  | 0.1149 | 0.1437 | 60 |  |
|  |  | 3 | M | 0.232 | 0.0302 | 180 |  | 0.1206 | 0.1508 | 60 |  |
|  |  | 4 | M | 0.235 | 0.0306 | 240 |  | 0.1222 | 0.1528 | 60 |  |
|  |  | 5 | F | 0.201 | 0.0261 | 120 |  | 0.1045 | 0.1307 | 60 |  |

TABLE 3

NX90 + NB33 testing and recovery time evaluation

| Group | Tested dose umol/kg (mpk) | Rat no. | Sex | Body weight (kg) | Fentanyl Dose/rat (mg) | Overdose induction (seconds) | Average overdose time (seconds) | Dose/rat NX90:NB33 (0.4 mg:0.4 mg) (mg) | ml of diluted NX90:NB33 IN | Total recovery time (seconds) | Average recovery time (seconds) |
|---|---|---|---|---|---|---|---|---|---|---|---|
| NX90 + NB33 1 | 0.16 + 0.16 | 1 | F | 0.319 | 0.0415 | 120 | 240 (4 min and 0 sec) | 0.0829 | 0.1037 | 180 | 114 ± 68 |
|  |  | 2 | M | 0.415 | 0.0540 | 240 |  | 0.1079 | 0.1349 | 180 |  |
|  |  | 3 | M | 0.385 | 0.0501 | 240 |  | 0.1001 | 0.1251 | 60 |  |
|  |  | 4 | M | 0.329 | 0.0428 | 360 |  | 0.0855 | 0.1069 | 30 |  |
|  |  | 5 | F | 0.320 | 0.0416 | 240 |  | 0.0832 | 0.1040 | 120 |  |
| NX90 + NB33 2 | 0.32 + 0.32 | 1 | M | 0.276 | 0.0359 | 360 | 264 (4 min and 24 sec) | 0.1435 | 0.1794 | 30 | 48 ± 16 |
|  |  | 2 | M | 0.259 | 0.0337 | 240 |  | 0.1347 | 0.1684 | 60 |  |
|  |  | 3 | F | 0.241 | 0.0313 | 240 |  | 0.1253 | 0.1567 | 60 |  |
|  |  | 4 | F | 0.222 | 0.0289 | 240 |  | 0.1154 | 0.1443 | 30 |  |
|  |  | 5 | F | 0.225 | 0.0293 | 240 |  | 0.1170 | 0.1463 | 60 |  |

TABLE 4

Data obtained by group and sex, regarding the average recovery time and the percentage of MPA (maximum possible analgesia) for NX + NB combinations

| Drug tested | Group no. | Dose mg/kg | Sex and number of rats | Average recovery time seconds |  | AT − 20 TFT* seconds |  | PT + 40 TFT* seconds |  | **MPA % average by sex | **MPA % average |
|---|---|---|---|---|---|---|---|---|---|---|---|
| 1 NB | 1. NB | 0.1 | 5 M | 5760 | 5400 | 2.57 | 2.62 | >40 | >40 | 100 | 100 |
|  |  |  | 5 F | 5040 |  | 2.67 |  | >40 |  | 100 |  |
| 2 NX:NB 1:1 | 2. NX:NB 1:1 | 0.1:0.1 | 3 M | 180 | 210 | 3.00 | 2.80 | 12.09 | 9.57 | 24.57 | 18.18 |
|  |  |  | 2 F | 240 |  | 2.61 |  | 7.04 |  | 11.86 |  |
| 3 NX:NB 1:1 | 3. NX:NB 1:1 | 0.05:0.05 | 3 M | 250 | 230 | 3.21 | 3.18 | 12.01 | 11.12 | 23.91 | 21.57 |
|  |  |  | 2 F | 210 |  | 3.15 |  | 10.24 |  | 19.24 |  |

TABLE 4-continued

Data obtained by group and sex, regarding the average recovery time and the percentage of MPA (maximum possible analgesia) for NX + NB combinations

| Drug tested | Group no. | Dose mg/kg | Sex and number of rats | Average recovery time seconds | | AT − 20 TFT* seconds | | PT + 40 TFT* seconds | | **MPA % average by sex | **MPA % average |
|---|---|---|---|---|---|---|---|---|---|---|---|
| 4 NX:NB 1:0.25 | 4. NX:NB | 0.1:0.025 | 2 M<br>3 F | 157.5<br>270 | 213.75 | 3.28<br>2.83 | 3.05 | 5.49<br>5.26 | 5.37 | 6.03<br>6.54 | 6.29 |
| 5 NX:NB 1:4 | 5. NX:NB | 0.1:0.4 | 2 M<br>3 F | 180<br>70 | 125 | 2.44<br>2.46 | 2.45 | 22.79<br>24.88 | 23.83 | 54.17<br>59.71 | 56.94 |

Predetermined cutoff time of 40 seconds was used
*AT − 20 TFT = ante therapeutic average TFT time (seconds), 20 minutes before fentanyl administration
*PT + 40 TFT = post therapeutic average TFT time (seconds), 40 minutes after fentanyl administration
**Percentage of maximum possible analgesia (% MPA) using the formula: % MPA = [(Test − Baseline)/(Cutoff − Baseline)] × 100%

Example 2. Safety Assessment of Combinations vs. Naloxone

Naloxone administration is associated with catecholamine release that is thought to be involved in pulmonary edema[6] and marked cardiovascular stimulation[17] the most prevalent side effects in overdose patients. These may lead to serious adverse events reported for doses as low as 2 μg/kg and raise a question what would be a safe dose in patients susceptible to naloxone induced withdrawal. Since naloxone-induced withdrawal could be characterized by activation of catecholaminergic neurons in the heart, we evaluated changes in the heart rate (HR) as a proxy for catecholamine surge.

Figure 2:
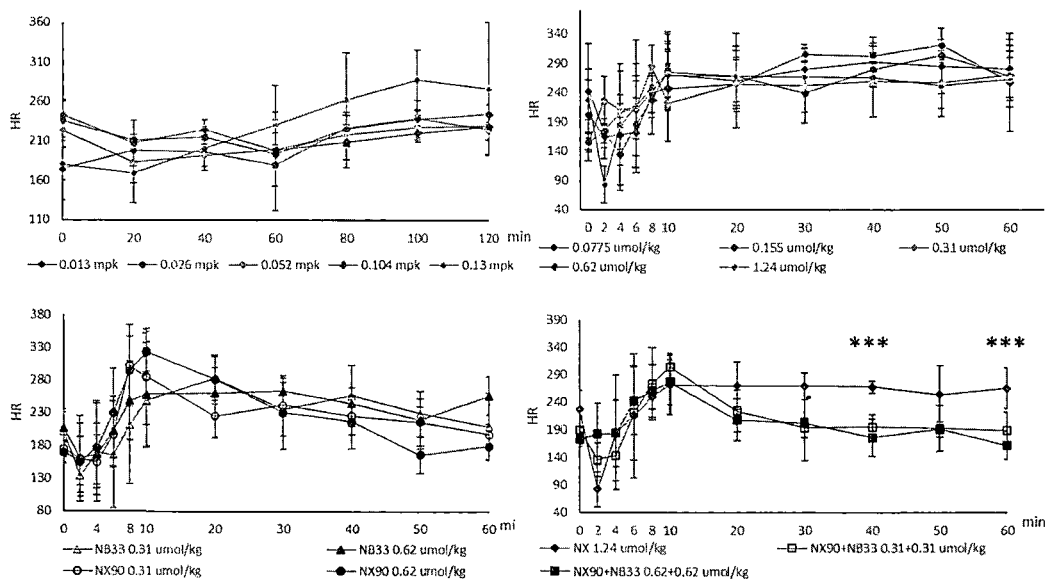
FIG. 2 is a collection four graphs showing the results of measurements of the effects of test substances on fentanyl driven overdoses in subject rats; and, FIG. 3 is a bar graph depicting dose rate comparisons of types and quantities of the test substances on OD reversal in subject rats.

FIG. 2 is a collection four graphs showing the results of measurements of the effects of test substances on fentanyl driven overdoses in subject rats. A. shows the mean heart rate (HR) for fentanyl treated animals. B. illustrates the mean HR for naloxone treated groups (n=5) in fentanyl driven OD. C. demonstrates mean heart rate (HR) for NB33 and NX90 treated groups (n=5) in fentanyl driven OD model. D. depicts the mean heart rate (HR) for the naloxone (1.24 umol/kg), NX90 (1.24 umol/kg) or NB33+NX90 (0.31+0.31 umol/kg and 0.62+0.62 umol/kg) treated groups (n=5) in fentanyl driven OD model.

Surprisingly, heart rate (HR) elevation in animals treated with combinations (e.g., NX90+NB33) at all doses, proved to be transient and returned to resting HR rates within 30 min unlike animals treated with Naloxone.

Example 3. —Dose Ratio Comparison

Figure 3:
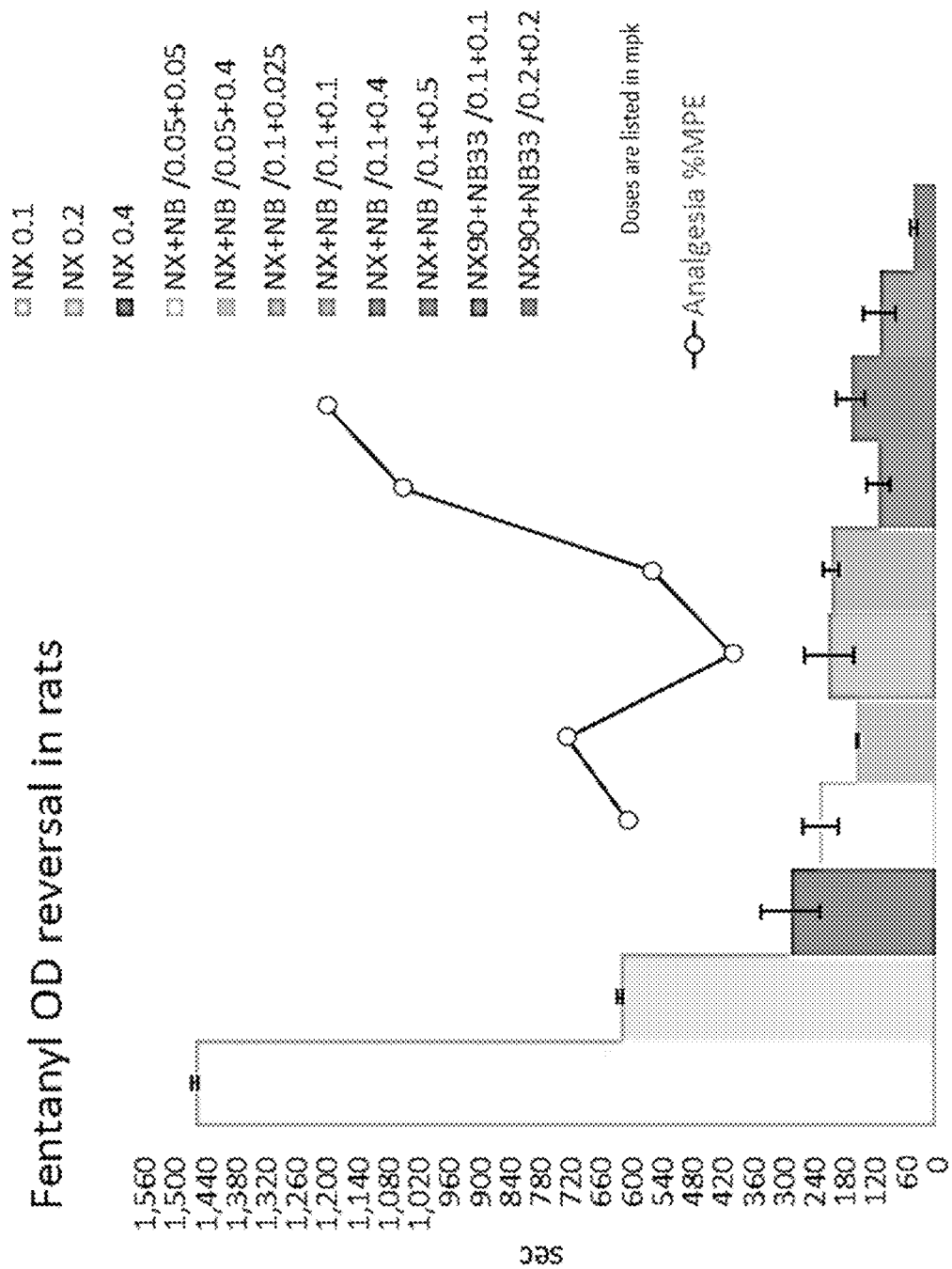

FIG. 3 is a bar graph depicting dose rate comparisons of types and quantities of the test substances on OD reversal in subject rats. Experiments were conducted to compare efficacy of doses of naloxone administered to rats given both separately and in combination with various ratios of doses of nalbuphine and naloxone, or NB-33 and NX-90. The bar graph in FIG. 3 displays the effect of various doses of naloxone alone or in combination with nalbuphine on fentanyl overdose reversal in rats. Reversal time is measured in seconds.

As mentioned above, NB-33 is a 3-hexadienoate derivative of Nalbuphine that converts to the parent drug in a biological matrix, while NX-90 is a 3-hexadienoate derivative of Naloxone that converts to the parent drug in a biological matrix. Surprisingly, lower doses of NB-33 (0.1 mpk, 0.2 mpk) in combination with 0.1 mpk of NX-90 reversed fentanyl overdose in rats in 1-2 minutes.

Thus, it is seen that the objects of the invention are efficiently obtained, although changes and modifications to the invention should be readily apparent to those having ordinary skill in the art, which changes would not depart from the spirit and scope of the invention as claimed.

We claim:

1. A remedial opioid overdose mixture comprising:
   naloxone in an amount ranging from about 0.022 mg/kg body weight to about 0.087 mg/kg body weight of the patient; and
   nalbuphine in an amount ranging from about 0.022 mg/kg body weight to about 0.087 mg/kg body weight of the patient;
   wherein the remedial mixture is effective to reverse an opioid overdose in a patient.

2. The remedial opioid overdose mixture of claim 1, wherein the remedial mixture is effective to reverse the overdose in the patient within three minutes.

3. A remedial opioid overdose mixture comprising:
   a therapeutically effective amount of NX-90 as an mu opioid receptor antagonist; and
   a therapeutically effective amount of NB-33 as an kappa opioid receptor agonist;
   wherein the remedial mixture is effective to reverse an opioid overdose in a patient, and
   wherein the therapeutically effective amount of NX-90 ranges about 0.022 mg/kg body weight to about 0.087 mg/kg body weight of the patient and wherein the therapeutically effective amount of NB-33 ranges from about 0.022 mg/kg body weight to about 0.087 mg/kg body weight of the patient.

4. The remedial opioid overdose mixture of claim 3, wherein the remedial mixture is effective to reverse the overdose in the patient within three minutes.

5. A method for reversing opioid overdose in a patent, comprising administering an effective amount of the remedial opioid mixture of claim 1 to a patient suffering from opioid overdose.

6. A method for reversing opioid overdose in a patent, comprising administering an effective amount of the remedial opioid mixture of claim 2 to a patient suffering from opioid overdose.

7. A method for reversing opioid overdose in a patent, comprising administering an effective amount of the remedial opioid mixture of claim 3 to a patient suffering from opioid overdose.

8. A method for reversing opioid overdose in a patent, comprising administering an effective amount of the remedial opioid mixture of claim 4 to a patient suffering from opioid overdose.

9. The method of claim 5, wherein the remedial opioid mixture is administered intranasally, intramuscularly, or by injection to the patient.

10. The method of claim 6, wherein the remedial opioid mixture is administered intranasally, intramuscularly, or by injection to the patient.

11. The method of claim 7, wherein the remedial opioid mixture is administered intranasally, intramuscularly, or by injection to the patient.

12. The method of claim 8, wherein the remedial opioid mixture is administered intranasally, intramuscularly, or by injection to the patient.

* * * * *